US012751637B2

(12) United States Patent
Proença et al.

(10) Patent No.: US 12,751,637 B2
(45) Date of Patent: Oct. 6, 2026

(54) METHOD FOR DETERMINING A PHYSIOLOGICAL PARAMETER USING A PPG SIGNAL WITH REDUCED INFLUENCE OF VENOUS PULSATILITY

(71) Applicant: CSEM Centre Suisse d'Electronique et de Microtechnique SA - Recherche et Développement, Neuchâtel (CH)

(72) Inventors: Martin Proença, Sugiez (CH); Philippe Renevey, Lausanne (CH); Damien Ferrario, La Tour-de-Peilz (CH); Guillaume Bonnier, Bussigny (CH)

(73) Assignee: CSEM Centre Suisse d'Electronique et de Microtechnique SA—Recherche et Développement, Neuchâtel (CH)

( * ) Notice: Subject to any disclaimer, the term of this patent is extended or adjusted under 35 U.S.C. 154(b) by 553 days.

(21) Appl. No.: 17/511,717

(22) Filed: Oct. 27, 2021

(65) Prior Publication Data

US 2022/0133165 A1 May 5, 2022

(30) Foreign Application Priority Data

Oct. 29, 2020 (EP) .................................... 20204672

(51) Int. Cl.
*A61B 5/024* (2006.01)
*A61B 5/00* (2006.01)

(52) U.S. Cl.
CPC ........ *A61B 5/02416* (2013.01); *A61B 5/6823* (2013.01); *A61B 5/6824* (2013.01)

(58) Field of Classification Search
None
See application file for complete search history.

(56) References Cited

U.S. PATENT DOCUMENTS 8,251,912 B2 8/2012 Shelley et al.
2006/0241506 A1 10/2006 Melker et al.
(Continued)

FOREIGN PATENT DOCUMENTS

CN 104605863 B 6/2019
WO 2007147069 A2 12/2007
(Continued)

OTHER PUBLICATIONS

Search Report issued in European Application No. 20204672 dated Apr. 14, 2021.
(Continued)

*Primary Examiner* — Shahdeep Mohammed
(74) *Attorney, Agent, or Firm* — McDonald Hopkins LLC

(57) ABSTRACT

A method for determining a physiological parameter, including: providing a PPG sensor device configured to measure a PPG signal; measuring a PPG signal on the user, the PPG signal containing at least two cardiac cycles; identifying PPG pulses from the PPG signal, each corresponding to a cardiac cycle and having a non-modulated component and a time-modulated component; for each PPG pulse, determining at least one venous-related feature indicative of the contribution of venous pulsatility to the time-modulated component of the PPG pulse; assigning a weighting factor to each pulse including calculating the weighting factor by using a weighting function including a mathematical operator inputted with the set of at least one venous-related feature; computing a weighted-average PPG pulse by using the PPG pulses and their respective weighting factors; and determining the physiological parameter by using the weighted-average PPG pulse.

18 Claims, 5 Drawing Sheets

(56) References Cited

U.S. PATENT DOCUMENTS

| | | | | |
|---|---|---|---|---|
| 2015/0196257 | A1 | 7/2015 | Yousefi et al. | |
| 2015/0282746 | A1 | 10/2015 | Yousefi et al. | |
| 2017/0086755 | A1* | 3/2017 | De Haan | A61B 5/7278 |
| 2017/0209055 | A1* | 7/2017 | Pantelopoulos | A61B 5/7203 |
| 2018/0085012 | A1* | 3/2018 | Wei | A61B 5/318 |
| 2018/0146869 | A1* | 5/2018 | Zhang | A61B 5/7264 |
| 2021/0401332 | A1* | 12/2021 | John | A61B 5/02116 |

FOREIGN PATENT DOCUMENTS

| | | | |
|---|---|---|---|
| WO | 2012009350 | A1 | 1/2012 |
| WO | 2016/154210 | A1 | 9/2016 |

OTHER PUBLICATIONS

Written Opinion issued in European Application No. 20204672 dated Apr. 14, 2021.

Solà, Josep, et al: "Parametric estimation of pulse arrival time: a robust approach to pulse wave velocity", Physiological Measurement, Jun. 3, 2009, pp. 603-615, IOP Publishing, printed in the UK.

Chiu, Christopher Y., et al: "Determination of pulse wave velocities with computerized algorithms", Determination of arterial pulse wave velocities, American Heart Journal, May 1991, pp. 1460-1470, vol. 121, No. 5.

Communication pursuant to Article 94(3) EPC issued in European Patent Application No. 21204800.3-1113 dated Jul. 18, 2025.

Kirk H. Shelley et al., "The detection of peripheral venous pulsation using the pulse oximeter as a plethysmograph", Journal of clinical monitoring, vol. 9, No. 4, Sep. 1, 1993, pp. 283-287, XP093146617.

Jesse Fine et al., "Sources of Inaccuracy in Photoplethysmography for Continuous Cardiovascular Monitoring", Biosensors, vol. 11, No. 4, Apr. 16, 2021, p. 126, XP093146613.

* cited by examiner

METHOD FOR DETERMINING A PHYSIOLOGICAL PARAMETER USING A PPG SIGNAL WITH REDUCED INFLUENCE OF VENOUS PULSATILITY

TECHNICAL DOMAIN

The present invention concerns a method for determining a physiological parameter using a photoplethysmography (PPG) signal with reduced influence of venous pulsatility.

RELATED ART

A PPG signal is acquired by illuminating a region of a user's body with a light source and measuring the transmitted light that has gone through the tissue (transmission mode) or that has been back-scattered by the tissue (reflectance mode) with a light receiver. The light interacts with the body mainly through scattering and absorption processes. The PPG signal corresponds to the amount of light that reaches the detector, i.e., the amount of light which is not absorbed or scattered away from the detector. The PPG signal comprises two components: a non-modulated component (often referred to as direct component, or DC) and a time-modulated component (often referred to as alternating component, or AC). The DC results from the interaction of the light with the non-pulsating blood and the tissue (muscle, bone, skin, etc.). The AC results from the interaction of the light with the pulsating blood. The AC is thus mainly influenced by arterial pulsatility and by venous pulsatility. Arterial pulsatility corresponds to cardio-synchronous changes in blood volume due to the dilation of the arteries resulting from cardiac activity. Venous pulsatility corresponds to cardio-synchronous changes in blood volume due to the dilation of the veins resulting from cardiac activity.

Consecutive pulses in a PPG signal are not necessarily affected by the same amount of venous pulsatility. For instance, factors such as respiration create an intrathoracic pressure gradient that modulates the venous return to the heart, which in turn modulates differently the amount of venous pulsatility in individual consecutive pulses. Other factors such as the muscle pump system of peripheral veins during activity, an increase in central venous pressure following a decrease in venous compliance, the compression of the vena cava or the effects of gravity, may also affect the amount of venous pulsatility by altering venous return.

Venous pulsatility typically induces blood volume changes of smaller amplitude than arterial pulsatility and is often considered negligible. However, factors such as the pressure applied onto the PPG sensor device against the body affect the amount of venous pulsatility and may let it become significant in some cases, e.g. when not enough pressure is applied. This is particularly true when measuring the PPG signal in reflectance mode. In such cases, separating the pulsatile arterial component from the pulsatile venous component in the measured PPG signal by source separation techniques is extremely complex, as both components originate from the same source (cardiac activity). However, separating both components, or at least obtaining a PPG signal with minimal venous pulsatility influence, is highly desirable for various applications.

Cardiovascular applications which aim at determining a physiological parameter related to the arterial system are generally based on the assumption that the AC of the PPG signal has arterial pulsatility as its only source. Examples of such applications are the estimation of physiological parameters such as blood pressure, blood pressure variations, blood oxygen saturation, perfusion index, stroke volume, stroke volume variations, cardiac output, or cardiac output variations. For instance, the estimation of blood pressure or blood pressure variations is typically based on the analysis of the morphology of the AC of the PPG signal, the latter being assumed to be made of the same physiological determinants as the underlying arterial pressure waveform.

The presence of venous pulsatility changes the morphology of the AC of the PPG signal and therefore adds a confounding factor to its relationship with the underlying arterial pressure waveform, thereby undermining the accuracy of the blood pressure estimation. Similarly, the estimation of blood oxygen saturation or the perfusion index by PPG signal analysis as performed by standard pulse oximeters is intrinsically based on the assumption that the changes in light absorption measured in the AC of the PPG signal are due to changes in oxygen saturation in the arterial blood only. The presence of venous pulsatility modifies the light absorption measured in the AC of the PPG signal and intrinsically invalidates this assumption, affecting the accuracy of the measurement.

The measurement of stroke volume (or any of its related parameters such as stroke volume variations, cardiac output, or cardiac output variations), generally relates an amplitude-related parameter of the AC of the PPG signal to stroke volume, based on the assumption that the amplitude of the PPG signal is related to the distension undergone by the arteries when the stroke volume is ejected into the arterial system. Here again, the presence of venous pulsatility invalidates this assumption as it may modify the amplitude of the AC of the PPG signal.

Several attempts at separating or removing the venous contribution from a PPG signal have been made in the past. For example, in US20150282746, a method is proposed based on the combination of a red signal and an infrared signal of a PPG sensor. The implementation of this solution has the drawback of requiring a dual-wavelength PPG sensor. Another approach is disclosed in US20150196257, where several mathematical filters are applied to a PPG signal in order to remove motion-related artifacts and other un-wanted components, including venous contribution, from the measured PPG signal.

SUMMARY

The present disclosure concerns a method for determining a physiological parameter, comprising the steps of:

- providing a PPG sensor device configured to measure a PPG signal comprising at least an arterial pulsatility component and a venous pulsatility component;
- using the PPG sensor device to measure a PPG signal on the user, the PPG signal containing at least two cardiac cycles;
- identifying PPG pulses from the PPG signal, each PPG pulse corresponding to a cardiac cycle and having a non-modulated component and a time-modulated component;
- for each identified PPG pulse, determining a set of at least one venous-related feature indicative of the contribution of venous pulsatility to the time-modulated component of the PPG pulse from at least a waveform parameter characterizing the shape of the PPG pulse;
- assigning a weighting factor to each PPG pulse, comprising calculating the weighting factor by using a weighting function comprising a mathematical operator inputted with said set of at least one venous-related feature;

computing a weighted-average PPG pulse by using the identified PPG pulses and the respective weighting factors; and determining the physiological parameter by using the weighted-average PPG pulse.

The method disclosed herein allows for determining a physiological parameter from a PPG signal with a reduced influence of venous pulsatility. The method is based on pulse morphology (pulse shape) analysis and can be applied to single-wavelength PPG signals.

SHORT DESCRIPTION OF THE DRAWINGS

Exemplar embodiments of the invention are disclosed in the description and illustrated by the drawings in which.

EXAMPLES OF EMBODIMENTS

Figure 1:
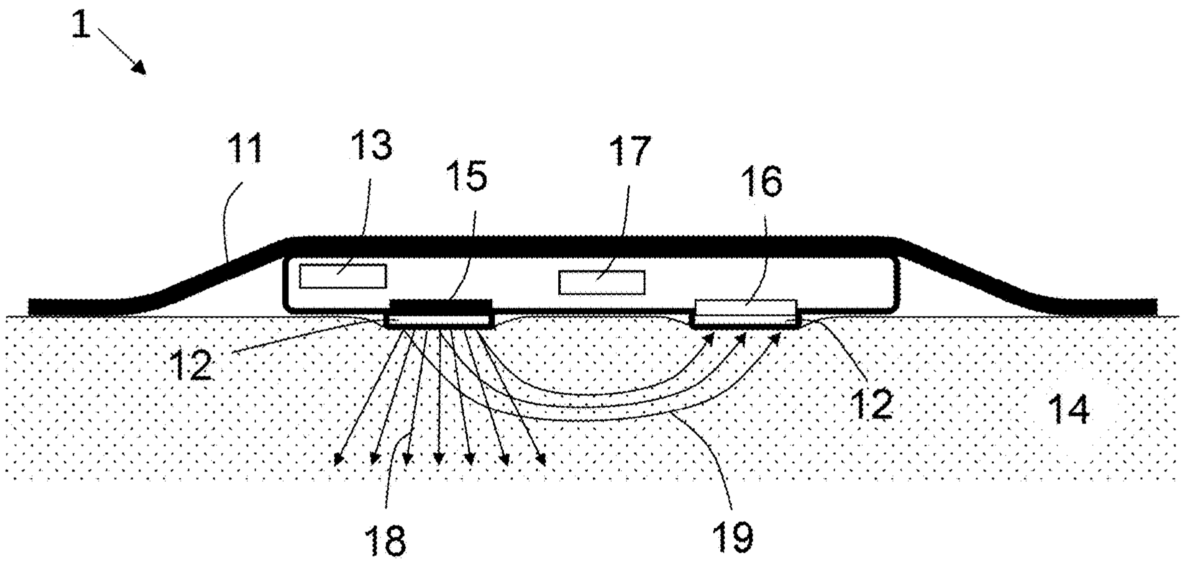
FIG. 1 illustrates schematically a reflection-based PPG sensor device comprising a light source and a light receiver.

FIG. 1 illustrates schematically a reflection-based PPG sensor device 1 for measuring a PPG signal of a tissue 14 (or body). The PPG sensor device 1 comprises a light source 15, such as a light-emitting diode, and a light receiver 16, such as a photodiode. The light source 15 and the light receiver 16 are on the same side of the tissue 14 to be measured. During a measurement, the light emitted from the light source 15 is either absorbed or scattered away 18 by the tissue 14 or back-scattered 19 through the tissue 14 to the light receiver 16. The PPG sensor device 1 can further comprise a motion sensor 17 delivering a motion signal representative of a motion of the user. The motion sensor can comprise an accelerometer, a gyroscope, a magnetometer or any suitable sensor configured for measuring a motion signal representative of a body motion of the user. Other configurations of the PPG sensor device 1 can be contemplated. For example, the PPG sensor device 1 can be a transmission-based PPG sensor.

Figure 2:
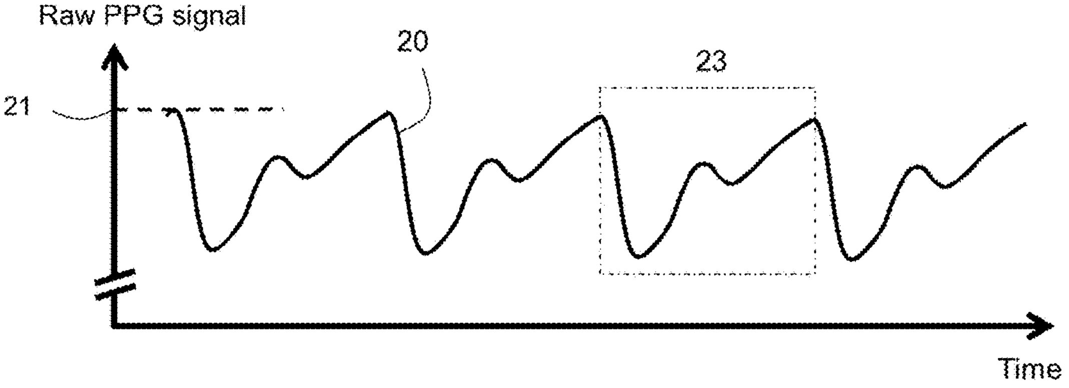
FIG. 2 illustrates schematically a PPG signal.

FIG. 2 shows a PPG signal 20 measured by the PPG sensor device 1. The PPG signal 20 comprises a DC 21 and an AC resulting from the interaction of the light with the pulsating blood. Here, the acronym "AC" means the time-modulated component of the PPG signal 20. Thus, in the following text the acronym "AC" should be read as "time-modulated component of the PPG signal 20". A signal segment containing a PPG pulse corresponding to a cardiac cycle is indicated by the numeral 23. By extension, in the following text the acronym "AC" should also be read as "time-modulated component of the PPG pulse" since the PPG pulse is a portion of the PPG signal 20. The time span represented in FIG. 2 comprises four cardiac cycles and the DC is represented as a constant baseline 21. It is understood that in general the DC level may evolve in time as a function of, for instance, changes in non-pulsatile blood content, the pressure applied on the PPG sensor, the user position, posture, or physical activity, or the ambient temperature. In absence of exogenous interferences (e.g., sensor detachment, strong motion artifacts, etc.), the normal frequency range of the DC level fluctuations can thus be defined in the sub-cardiac frequency range, typically below 0.5 Hz, corresponding to an extremely low heart rate of 30 beats per minute.

Figure 3:
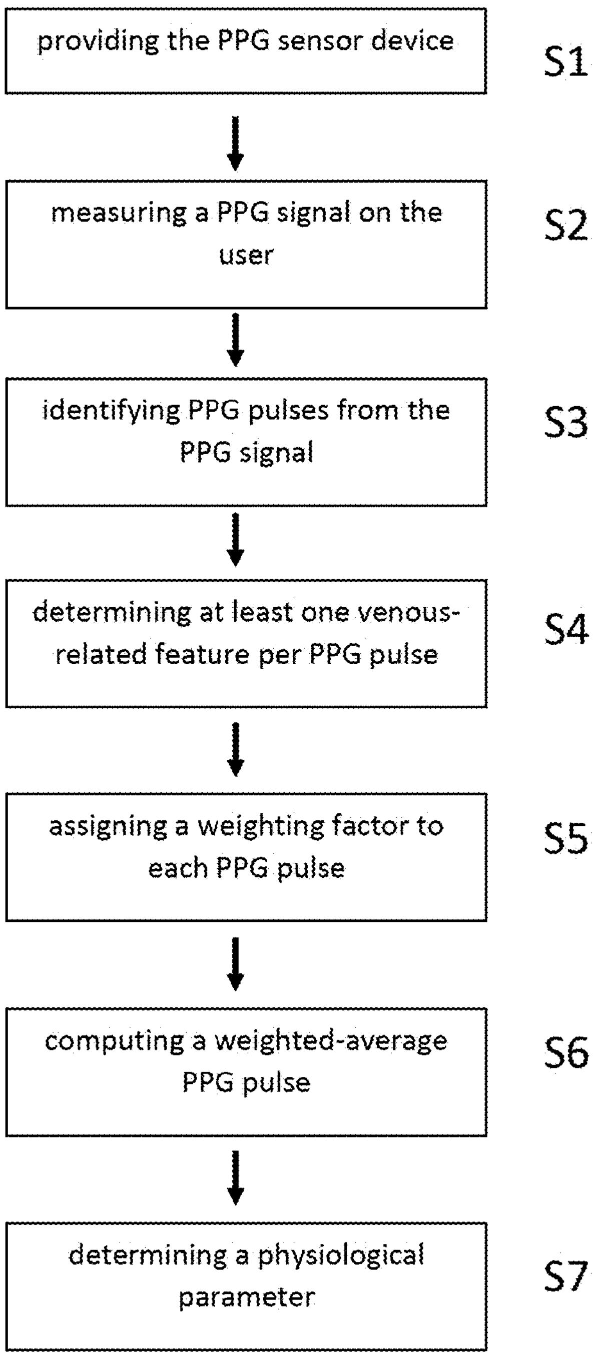
FIG. 3 illustrates a method for determining a physiological parameter of a user, according to an embodiment.

According to an embodiment illustrated in FIG. 3, a method for determining a physiological parameter of a user, comprises the steps of:

providing the PPG sensor device 1 configured to measure the PPG signal 20 comprising at least an arterial pulsatility component and a venous pulsatility component (S1);

using the PPG sensor device 1 to measure a PPG signal 20 on the user, the PPG signal 20 containing at least two cardiac cycles (S2);

identifying PPG pulses 23 from the PPG signal 20, each PPG pulse 23 corresponding to a cardiac cycle and having a non-modulated component and a time-modulated component (S3);

for each PPG pulse 23, determining at least one venous-related feature indicative of the contribution of venous pulsatility to the time-modulated component of the PPG pulse (S4), wherein the venous-related feature is determined from at least a waveform parameter characterizing the shape of the PPG pulse;

assigning a weighting factor to each pulse 23, comprising calculating the weighting factor by using a weighting function comprising a mathematical operator inputted with said set of at least one venous-related feature (S5);

computing a weighted-average PPG pulse by using the PPG pulses 23 and their respective weighting factors (S6); and determining a physiological parameter by using the weighted average PPG pulse (S7).

The PPG sensor device 1 can be provided embedded in or attached to a wearable textile support 11 (see FIG. 1) destined to be worn by the user. The wearable textile support 11 can comprise a patch-like support, a belt, a strap, a garment, or any other suitable wearable textile support.

The PPG sensor device 1 can further be provided as a standalone sensor.

In an embodiment, measuring the PPG signal 20 on the user is performed by placing the PPG sensor device 1 at the thorax or the upper arm, above the level of the seventh intercostal space. By analysing PPG pulses 23 from the PPG signal 20 measured at the upper thorax and the upper arms (above the level of the seventh intercostal space), the present inventors have found that a set of one or more waveform parameters, wherein each waveform parameter characterizes the shape of the PPG pulse and is related to the amount of venous pulsatility in each PPG pulse 23 can be calculated. Using said features, it is possible to obtain a weighted-average PPG pulse where the influence of venous pulsatility is reduced.

Respiration-induced deformation of the thoracic cage may affect the pressure applied onto the sensor, especially when the sensor is placed onto a body part that is particularly sensitive to such deformation. The mechanical modification of the interface between the sensor and the tissues may affect the signal physiologically by modulating the venous blood flow and optically by changing the optical properties of the interface. The method disclosed herein allows for decreasing the influence of venous pulsatility in the measured PPG signal. For example, reliable PPG signals with reduced influence of venous pulsatility can be obtained in the upper thoracic area.

The PPG sensor device 1 can further be provided such that a controlled pressure is applied between the PPG sensor device 1 and the tissue 14 (for example skin), such that substantially the totality of the light emitted by the light source 15 is transmitted to the tissue 14.

In one aspect, the wearable textile support 11 is configured to apply the controlled pressure between the PPG sensor device 1 and the tissue 14. To that end, the wearable textile support 11 can be at least an elastic (stretchy) portion.

In another aspect, the PPG sensor device 1 can be configured to apply the controlled pressure between the PPG sensor device 1 and the tissue 14. For example, the PPG sensor device 1 can comprise a (preferably transparent) protrusion 12 (see FIG. 1) extending between the PPG sensor device 1 and the tissue 14 (or any type of mechanical device) when the PPG sensor device 1 contacts the tissue 14.

In yet another aspect, the controlled pressure can be applied by the user itself, or by gravity.

Because arterial blood pressure is higher than venous blood pressure in the human body, applying a controlled pressure that is above venous pressure, but below arterial pressure, can decrease the influence of venous pulsatility in the PPG signal 20 and provide a PPG signal that is more representative of arterial pulsatility. The applied controlled pressure can typically be between 0.6 kPa and 10.7 kPa (between about 5 and 80 mmHg). Preferably, the applied controlled pressure can be between 1.3 kPa and 8 kPa (between about 10 and 60 mmHg).

In one aspect, the step of identifying each PPG pulse 23 from the PPG signal 20 can be performed by any one of the following methods: detecting the onset of the identified PPG pulse 23 from the maximum of its first time-derivative; detecting the onset of the identified PPG pulse 23 as the foot of the identified PPG pulse 23; detecting the onset of the identified PPG pulse 23 from the maximum of its second time-derivative; detecting the onset of the identified PPG pulse 23 as the maximum of the identified PPG pulse 23; detecting the onset of the identified PPG pulse 23 as the partial amplitude of the upstroke of the identified PPG pulse 23; detecting the onset of the identified PPG pulse 23 by using the intersecting tangent method (see Reference 1: Chiu, Y. C., et. al., "Determination of pulse wave velocities with computerized algorithms", American Heart Journal, 1991 May; 121(5):1460-70).

The step of identifying each PPG pulse 23 from the PPG signal 20 can further be performed by fitting a parametric model such as a hyperbolic tangent or a Morlet wavelet on the pulse upstroke (see Reference 2: Josep Sola, et. al., "Parametric estimation of pulse arrival time: a robust approach to pulse wave velocity", Physiol. Meas. 2009 July; 30(7):603-15). The step of identifying each PPG pulse 23 from the PPG signal 20 can further be performed by parametric estimation of its pulse arrival time (see Reference 2).

Figure 4:
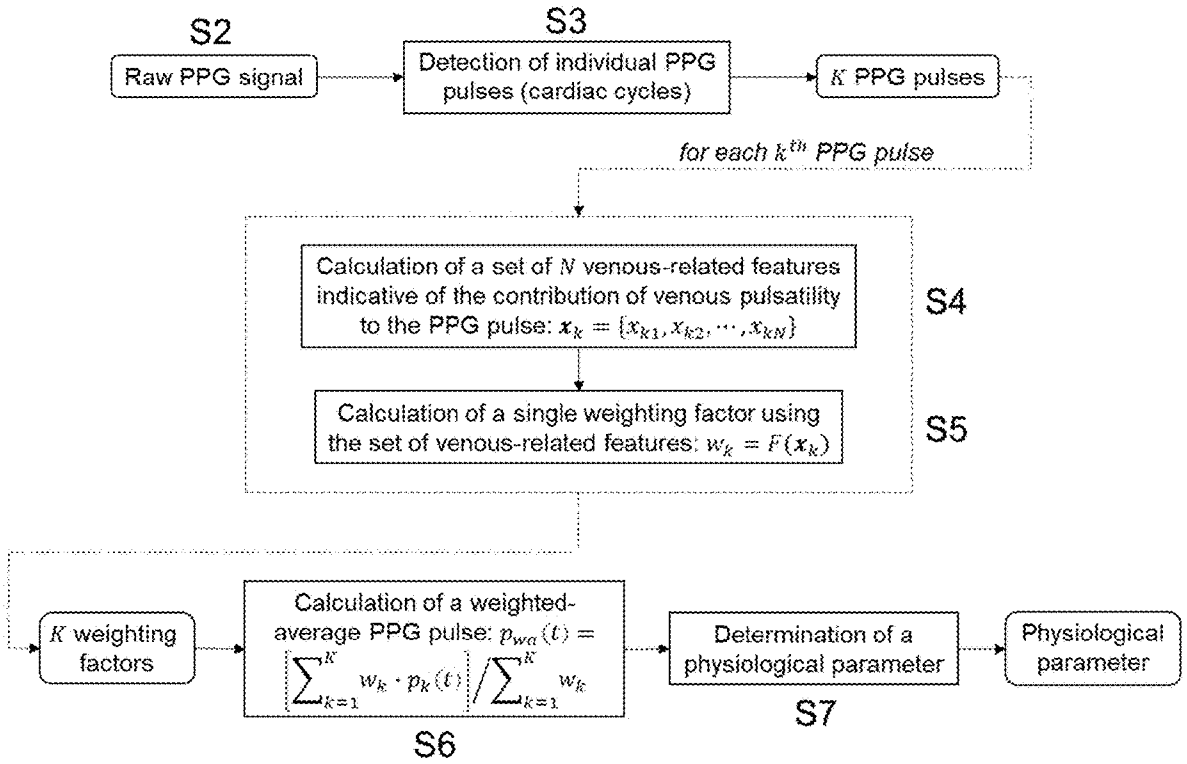
FIG. 4 illustrates a method for determining a physiological parameter of a user, according to a specific embodiment.

FIG. 4 illustrates the method for determining a physiological parameter of a user, according to a specific embodiment. In particular, the step of determining at least one venous-related feature (S4) comprises, for each PPG pulse 23, calculating a plurality of venous-related features. In other words, the step of determining at least one venous-related feature (S4) comprises, for each $k^{th}$ PPG pulse 23 ($k \in \{1, \ldots, K\}$), calculating a set $x_k$ of N ($N \geq 1$) venous-related features: $x_k = \{x_{k1}, x_{k2}, \ldots, x_{kN}\}$.

The venous-related features determined in the step S4 of the methods described above with reference to FIGS. 3 and 4 are determined from at least one waveform parameter characterizing the shape of the PPG pulse. The waveform parameter can comprise an amplitude of the pulse, a time lapse within the pulse or an area under the pulse. The waveform parameter can be extracted from the PPG pulse or the time-derivatives of the PPG pulse. Determining the venous-related features can also comprise performing mathematic operations using any one of said waveform parameters.

Figure 5:
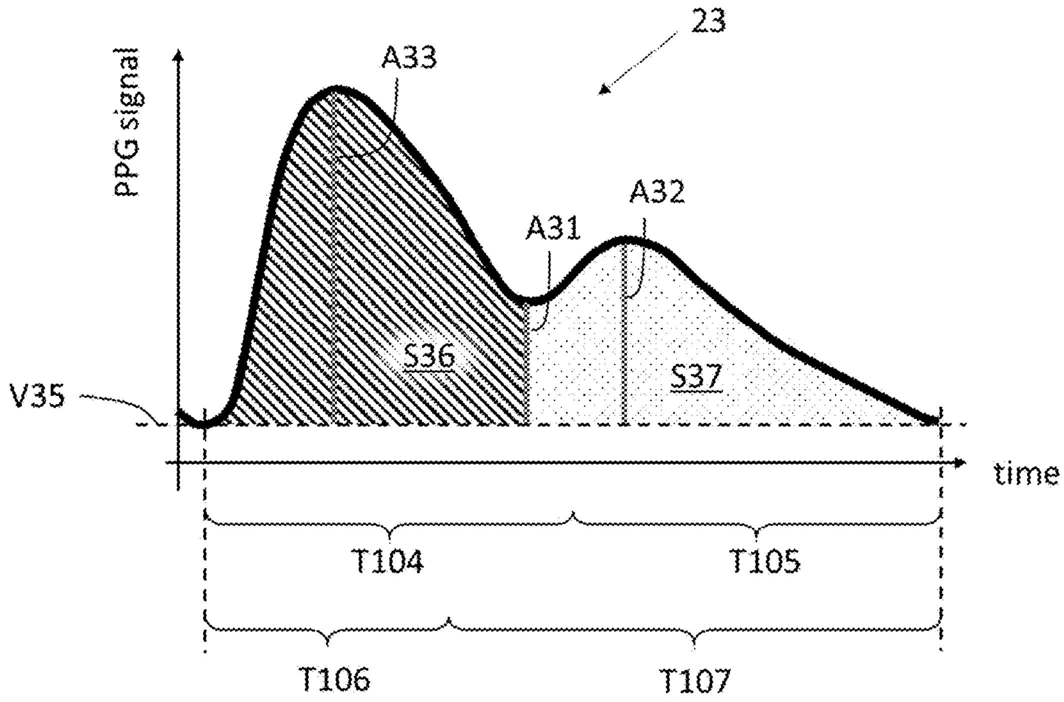
FIG. 5 illustrates schematically a PPG pulse indicating examples of pulse morphology parameters.

FIG. 5 illustrates schematically a typical PPG pulse 23, where several waveform parameters (A31, A32, A33, T104, T105, T106, T107, S36, S37, V35) which can be related with venous contribution to the time modulated component of the PPG pulse are indicated. For convenience of the representation, in FIG. 5 the pulse 23 has been inverted (turned upside down) with respect to the PPG signal illustrated in FIG. 2.

Examples of possible venous-related features determined in step S4 of the methods described above can comprise (see FIG. 5) any one of:

- the amplitude of the diastolic peak A32 of the PPG pulse 23 divided by the amplitude of the systolic peak A33;
- the amplitude of the dicrotic notch A31 of the PPG pulse 23 divided by the amplitude of the systolic peak A33;
- the post-dicrotic notch area S37 of the PPG pulse 23 divided by the pre-dicrotic notch area S36;
- the area under the PPG pulse 23 in the time window covering the second half of the pulse duration T105, divided by the area under the PPG pulse 23 in the time window covering the first half of the pulse duration T104; or
- the area under the PPG pulse 23 in the time window covering the last two thirds of the pulse duration T107, divided by the area under the PPG pulse 23 in the time window covering the first third of the pulse duration T106.

A normalized PPG pulse 103 can be obtained by subtracting the end-diastolic value V35 from the PPG pulse 23, then dividing it by the amplitude of the systolic peak A33.

Figure 6:
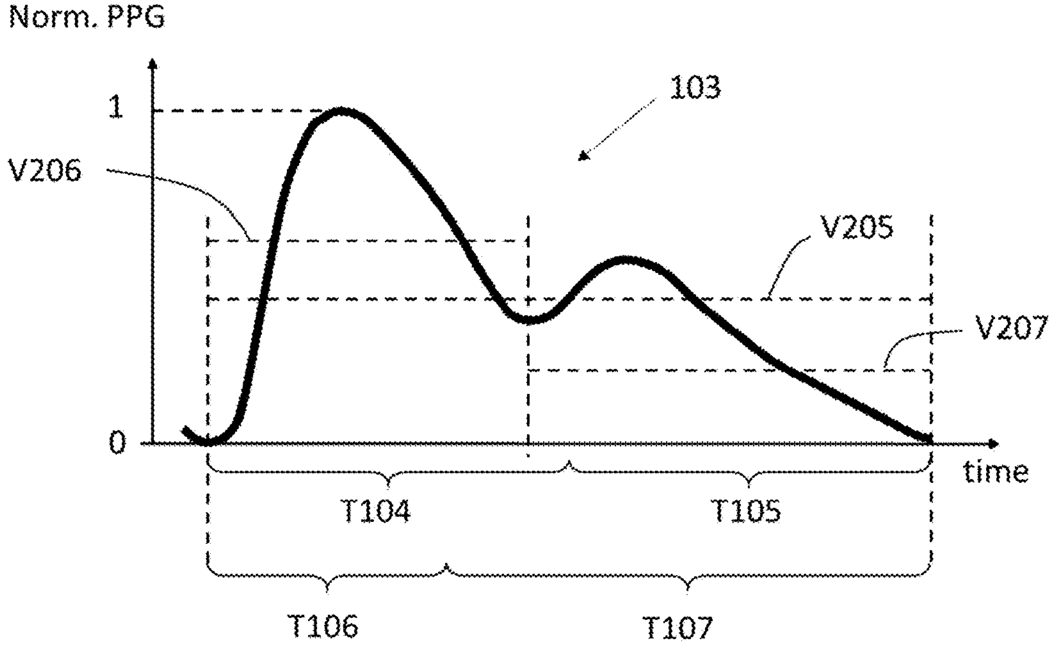
FIG. 6 illustrates schematically a normalized PPG pulse indicating other examples of pulse morphology parameters.

FIG. 6 schematically represents a normalized PPG pulse 103 and indicates additional waveform parameters (V205, V206, V207), which can be used to define other possible venous-related features. Other possible venous-related features can comprise:

- the mean value V205 of the normalized PPG pulse 103;
- the mean value V207 of the normalized PPG pulse 103 in the post-dicrotic notch portion divided by the mean value V206 of the normalized PPG pulse 103 in the pre-dicrotic notch portion of the normalized PPG pulse 103;
- the mean value of the normalized PPG pulse 103 in the time window covering the second half of the pulse duration T105 divided by the mean value of the normalized PPG pulse 103 in the time window covering the first half of the pulse duration T104; or
- the mean value of the normalized PPG pulse 103 in the time window covering the last two thirds of the pulse duration T107, divided by the average value of the normalized PPG pulse 103 in the time window covering the first third of the pulse duration T106.

Figure 7:
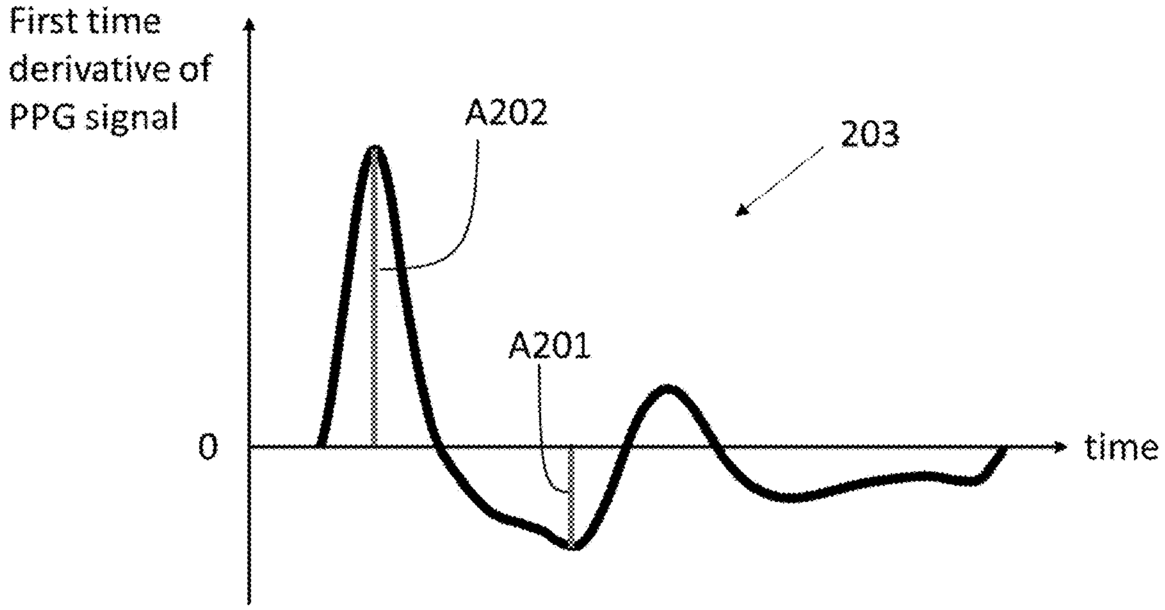
FIG. 7 illustrates schematically the first time-derivative of a PPG pulse indicating other examples of pulse morphology parameters.

FIG. 7 schematically represents the first time-derivative 203 of a PPG pulse 23 and indicates additional waveform parameters (A201, A202) which can be used to define other possible venous-related features. Other possible venous-related features can comprise the amplitude of the pre-dicrotic notch local minimum A201 of the first time-derivative 203 of the PPG pulse 23 divided by the amplitude of the first pre-dicrotic notch local maximum A202.

Another example of venous-related feature (not shown) can comprise the amplitude of the pre-dicrotic notch local minimum of the first time-derivative of the normalized PPG pulse 103.

Figure 8:
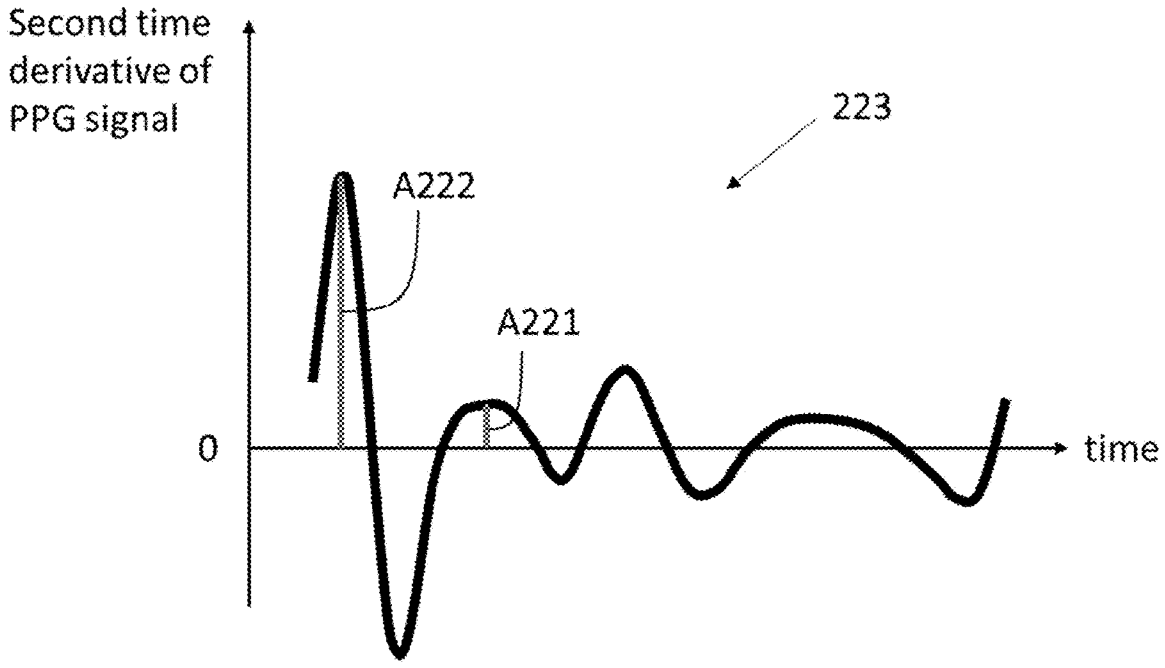
FIG. 8 illustrates schematically the second time-derivative of a PPG pulse indicating other examples of pulse morphology parameters.

FIG. 8 schematically represents the second time-derivative 223 of a PPG pulse 23. FIG. 8 also indicates additional waveform parameters (A221, A222) which can be used to define other possible venous-related features, such as the amplitude of the second pre-dicrotic notch local maximum A221 of the second time-derivative 223 of the PPG pulse 23 divided by the amplitude the first pre-dicrotic notch local maximum A222.

Another example of venous-related feature (not shown) can comprise the amplitude of the second pre-dicrotic notch local maximum of the second time-derivative of the normalized PPG pulse 103.

The relationship between the venous-related features described herein and the influence of venous pulsatility in the acquired PPG signals has been empirically established by the inventors by comparing the morphology of PPG signals with that of intra-arterial blood pressure waveforms. Although both waveforms are not measures of the exact same physiological phenomenon, they contain the same physiological determinants, provided that venous pulsatility is negligible. The examples of venous-related features determined using the PPG pulse waveform parameters presented above, were found to be good mathematic indicators of the correlation between the PPG waveform and the intra-arterial blood pressure waveform, on a pulse by pulse basis. The present method allows for improving the accuracy of the PPG-based calculation of physiological parameters, by producing a weighted average of several pulses, wherein PPG pulses presenting waveforms indicative of high venous pulsatility are assigned a lower weight in the average.

Other PPG pulse waveform parameters, or combinations thereof, can be identified, where said parameters correlate with venous pulsatility contribution to the PPG signal and thus correspond to the notion of "venous-related features" as disclosed here.

The step of determining at least one venous-related feature (S4) can further comprise calculating at least one transformed venous-related feature by applying a transformation function to at least one venous-related feature. The transformation function can comprise a logarithm, a polynomial regression, or any type of mathematical operation.

The step of determining a least one venous-related feature (S4) can further comprise determining a plurality of venous-related features. At least one combined venous-related feature can then be calculated comprising a combination of any one of the determined venous-related features. For example, determining at least one venous-related feature can comprise calculating a combined venous-related feature $x_{k3}$ from at least two venous-related features, for example: $x_{k3}=x_{k1}\cdot x_{k2}$.

A combined venous-related feature can further be obtained by combining at least two transformed venous-related features. Alternatively, a combined venous-related feature can be obtained by applying the transformation function to the combination of any one of the venous-related features.

The step of assigning a weighting factor can comprise using the set of at least one venous-related feature $x_k$ to calculate a weighting factor $w_k$ for each $k^{th}$ identified PPG pulse 23 such that $w_k=F(x_k)$, where F is a weighting function that can comprise any type of mathematical operator that takes as input a set of one or more venous-related feature $x_k$ and outputs a single weighting factor $w_k$.

In one aspect, the weighting function F is a classifier configured such that the value of the weighting factor $w_k$ depends on the value of each of the various venous-related features from the set of at least one venous-related feature $x_k$.

In another aspect, the weighting factor $w_k$ can be determined by using a linear or non-linear regression of one or more venous-related features $x_k$.

In one aspect, the at least one venous-related feature correlates positively or negatively with the contribution of venous pulsatility to the AC of each PPG pulse 23. In other words, the at least one venous-related feature can have a value that decreases with an increasing contribution of the venous pulsatility to the AC of each PPG pulse 23, or a value that increases with an increasing contribution of venous pulsatility to the AC of each PPG pulse 23.

Examples of venous-related features which correlate positively with the contribution of venous pulsatility to the AC of the PPG signal (feature increases when venous pulsatility increases) can include:

- the amplitude of the diastolic peak A32 of the PPG pulse 23 divided by the amplitude of the systolic peak A33;
- the amplitude of the dicrotic notch A31 of the PPG pulse 23 divided by the amplitude of the systolic peak A33;
- the post-dicrotic notch area S37 of the PPG pulse 23 divided by the pre-dicrotic notch area S36; or
- the mean value V205 of the normalized PPG pulse 103.

Examples of venous related features which correlate negatively with the contribution of venous pulsatility to the AC of the PPG signal (feature decreases when venous pulsatility increases) can include:

- the amplitude of the pre-dicrotic notch local minimum A201 of the first time-derivative 203 of the PPG pulse 23 divided by the amplitude of the first pre-dicrotic notch local maximum A202; or
- the amplitude of the second pre-dicrotic notch local maximum A221 of the second time-derivative 223 of the PPG pulse 23 divided by the amplitude the first pre-dicrotic notch local maximum A222.

In particular, each venous-related feature in the set of one or more venous-related features $x_k$ can be configured such that its value correlates positively or negatively with the contribution of venous pulsatility to each $k^{th}$ identified PPG pulse 23.

In order to give more weight to the identified PPG pulses 23 with low contribution of venous pulsatility to their AC, the weighting function F is configured such that an increase in the value of a venous-related feature that correlates positively with the contribution of venous pulsatility to the AC of the $k^{th}$ identified PPG pulse 23 makes the value of the weighting factor $w_k$ decrease, whereas an increase in the value of a venous-related feature that correlates negatively with the contribution of venous pulsatility to the AC of the $k^{th}$ identified PPG pulse 23 makes the value of the weighting factor $w_k$ increase.

In an example where the set of venous-related features comprises one single feature (i.e., $x_k=\{x_{k1}\}$) and where $x_{k1}$ is the amplitude of the diastolic peak 32 of the PPG pulse 23 divided by the amplitude of the systolic peak 33, the weighting factor $w_k$ of each $k^{th}$ identified PPG pulse can for instance be $w_k=1/x_{k1}$. Indeed, as the feature $x_{k1}$ correlates positively with the contribution of venous pulsatility, the weighting factor $w_k$ is calculated in such a way that its value decreases when $x_{k1}$ increases.

In another example, the set of venous-related features comprises two features (i.e., $x_k=\{x_{k1},x_{k2}\}$), where $x_{k1}$ is the amplitude of the pre-dicrotic notch local minimum of the first time-derivative of the normalized PPG pulse 103 and $x_{k2}$ is the amplitude of the second pre-dicrotic notch local maximum of the second time-derivative of the normalized PPG pulse 103, the weighting factor $w_k$ can for instance be $[\alpha+\log(x_{k2})]$, with a equal to 0 if $x_{k1}$ is below a predetermined threshold, or 1 if $x_{k1}$ is above said threshold. In this example where both venous-related features correlate negatively with the contribution of venous pulsatility, the weighting factor is calculated in such a way that its value increases when $x_{k1}$ or $x_{k2}$ increase.

The step of computing a weighted-average PPG pulse (S6) can comprise using the weighting factors $w_k$ to calculate a weighted-average PPG pulse. The influence of PPG pulses with high contribution of venous pulsatility to their AC can be minimized as their corresponding weighting factors are low. More specifically, if $p_k(t)$ represents the $k^{th}$ identified PPG pulse 23 in the measured PPG signal 20 and $p_{wa}(t)$ the weighted-average PPG pulse, then $p_{wa}(t)$ can be obtained by using Equation 1:

$$p_{wa}(t)=\left[\sum\nolimits_{k=1}^{K} w_k\cdot p_k(t)\right]\Big/\sum\nolimits_{k=1}^{K} w_k. \quad (1)$$

The step of determining a physiological parameter (S7) comprises using the resulting weighted-average PPG pulse $p_{wa}(t)$ for estimating a physiological parameter in an application where the PPG pulse is preferably free of venous pulsatility influence.

In an embodiment, the PPG sensor device 1 further comprises a processing module 13 configured to determine a physiological parameter by using the method described herein.

The present disclosure further concerns a non-transitory computer readable medium storing a program causing a computer to execute the method described above for determining a physiological parameter of a user.

In an embodiment, the processing module 13 is configured to run the computer program.

REFERENCE NUMERAL USED IN THE FIGURES

1 PPG sensor device
11 textile support
12 protrusion
13 processing module
14 tissue
15 light source
16 light receiver
17 motion sensor
18 absorbed or scattered away light
19 back-scattered light
20 PPG signal
21 DC
23 PPG pulse
A31 dicrotic notch amplitude
A32 diastolic peak amplitude
A33 systolic peak amplitude
V35 end-diastolic value
S36 pre-dicrotic notch area
S37 post-dicrotic notch area
T104 time window covering the first half of the pulse duration T105 time window covering the second half of the pulse duration
T106 time window covering the first third of the pulse duration
T107 time window covering the last two thirds of the pulse duration
103 normalized PPG pulse
V205 mean value of normalized PPG pulse
V206 mean value of the normalized PPG pulse in the pre-dicrotic notch portion
V207 mean value of the normalized PPG pulse in the post-dicrotic notch portion
203 first time derivative of PPG pulse
A201 amplitude of the pre-dicrotic notch local minimum of the first time-derivative
A202 amplitude of the first pre-dicrotic notch local maximum of the first time derivative
223 second time-derivative of PPG pulse
A221 amplitude of the second pre-dicrotic notch local maximum of the second time-derivative
A222 amplitude the first pre-dicrotic notch local maximum of the second time-derivative
F weighting function
$p_k(t)$ $k^{th}$ identified PPG pulse
$p_{wa}(t)$ weighted-average PPG pulse
$x_k$ set of venous-related features of the $k^{th}$ identified PPG pulse
$c_{k1}, \ldots, x_{kN}$ venous-related features 1 to N of the $k^{th}$ identified PPG pulse
$w_k$ weighting factor of the $k^{th}$ identified PPG pulse

The invention claimed is:

1. A method for determining a physiological parameter, comprising the steps of:

providing a photoplethysmography (PPG) sensor device configured to measure a single PPG signal comprising a non-modulated component and a time-modulated component, wherein the time-modulated component comprises at least an arterial pulsatility component and a venous pulsatility component;

using the PPG sensor device to measure the single PPG signal on a user, the single PPG signal containing at least two cardiac cycles;

identifying individual PPG pulses from the single PPG signal, each individual PPG pulse corresponding to a cardiac cycle;

for each individual PPG pulse, determining a set of at least one venous pulse feature indicative of the contribution of venous pulsatility to the time-modulated component of the individual PPG pulse from at least a waveform parameter characterizing a shape of the individual PPG pulse;

assigning a weighting factor to each pulse, comprising calculating the weighting factor by using a weighting function comprising a mathematical operator inputted with said set of at least one venous pulse feature;

computing a weighted-average PPG pulse by using the individual PPG pulses and their respective weighting factors; and determining the physiological parameter by using the weighted-average PPG pulse.

2. The method according to claim 1, wherein the venous pulse feature comprises an amplitude of the diastolic peak of the individual PPG pulse divided by an amplitude of the systolic peak.

3. The method according to claim 1, wherein determining at least one venous pulse feature comprises determining a plurality of venous pulse features; and obtaining at least one combined venous pulse feature by combining any one of said plurality of venous pulse features.

4. The method according to claim 1, wherein the weighting function comprises a classifier configured such that a value of the weighting factor depends on a value of said at least one venous pulse feature.

5. The method according to claim 1, wherein the weighting function corresponds to an inverse of an amplitude of the diastolic peak of the individual PPG pulse divided by an amplitude of the systolic peak.

6. The method according to claim 1, wherein the single PPG signal is measured at a thorax or an upper arm, above a level of a seventh intercostal space.

7. The method according to claim 1, wherein the venous pulse feature comprises any one of, or a combination of, an amplitude of the dicrotic notch of the individual PPG pulse divided by an amplitude of the systolic peak;

a post-dicrotic notch area of the individual PPG pulse divided by a pre-dicrotic notch area;

an area under the individual PPG pulse in a time window covering the second half of the pulse duration, divided by the area under the individual PPG pulse in a time window covering the first half of the pulse duration; or the area under the individual PPG pulse in a time window covering the last two thirds of the pulse duration, divided by the area under the individual PPG pulse in a time window covering the first third of the pulse duration.

8. The method according to claim 1, wherein each venous pulse feature in the set of at least one venous pulse feature correlates positively or negatively with the contribution of venous pulsatility to the single PPG signal.

9. The method according to claim 8, wherein the weighting function is configured such that an increase in a value of a venous pulse feature that correlates positively with the contribution of venous pulsatility to the single PPG signal makes the value of the weighting factor to decrease, whereas an increase in the value of said at least one venous pulse feature that correlates negatively with the contribution of venous pulsatility to the single PPG signal makes the value of the weighting factor to increase.

10. The method according to claim 1, comprising computing a normalized PPG pulse by subtracting an end-diastolic value from the individual PPG pulse to obtain a subtracted PPG pulse and dividing the subtracted PPG pulse by an amplitude of the systolic peak; and wherein said at least one venous pulse feature is determined from at least a waveform parameter of the normalized PPG pulse.

11. The method according to claim 10, wherein the venous pulse feature comprises any one of, or a combination of, a mean value of the normalized PPG pulse;

the mean value of the normalized PPG pulse in a post-dicrotic notch portion divided by the mean value of the normalized PPG pulse in a pre-dicrotic notch portion of the normalized PPG pulse;

the mean value of the normalized PPG pulse in a time window covering the second half of the pulse duration divided by the mean value of the normalized PPG pulse in a time window covering the first half of the pulse duration; or the mean value of the normalized PPG pulse in a time window covering the last two thirds of the pulse duration, divided by an average value of the normalized PPG pulse in a time window covering the first third of the pulse duration.

12. The method according to claim 1, comprising computing a first time-derivative of the individual PPG pulse; and wherein said at least one venous pulse feature is determined from at least a waveform parameter of the first time-derivative.

13. The method according to claim 12, wherein the venous pulse feature comprises an amplitude of the pre-dicrotic notch local minimum of the first time-derivative divided by an amplitude of the first pre-dicrotic notch local maximum.

14. The method according to claim 1, comprising computing a second time-derivative of the individual PPG pulse; and wherein said at least one venous pulse feature is determined from at least a waveform parameter of the second time-derivative.

15. The method according to claim 14, wherein the venous pulse feature comprises an amplitude of the second pre-dicrotic notch local maximum of the second time-derivative divided by an amplitude the first pre-dicrotic notch local maximum.

16. A non-transitory computer readable medium storing a program causing a computer to execute a method comprising:

using a PPG sensor device to measure a single PPG signal on a user, the single PPG signal comprising at least an arterial pulsatility component and a venous pulsatility component, the single PPG signal containing at least two cardiac cycles;

identifying individual PPG pulses from the single PPG signal, each individual PPG pulse corresponding to a cardiac cycle and having a non-modulated component and a time-modulated component;

for each individual PPG pulse, determining a set of at least one venous pulse feature indicative of the contribution of venous pulsatility to the time-modulated component of the individual PPG pulse from at least a waveform parameter characterizing a shape of the individual PPG pulse;

assigning a weighting factor to each pulse, comprising calculating the weighting factor by using a weighting function comprising a mathematical operator inputted with said set of at least one venous pulse feature;

computing a weighted-average PPG pulse by using the individual PPG pulses and their respective weighting factors; and determining the physiological parameter by using the weighted-average PPG pulse.

17. A photoplethysmography (PPG) sensor device comprising a light source and a light receiver and configured to measure a single PPG signal comprising a non-modulated component and a time-modulated component, wherein the time-modulated component comprises at least an arterial pulsatility component and a venous pulsatility component; the PPG sensor device further comprising a processing module configured to execute a method comprising:

measuring the single PPG signal on a user, the single PPG signal containing at least two cardiac cycles;

identifying individual PPG pulses from the single PPG signal, each individual PPG pulse corresponding to a cardiac cycle and having the non-modulated component and the time-modulated component;

for each individual PPG pulse, determining a set of at least one venous pulse feature indicative of the contribution of venous pulsatility to the time-modulated component of the individual PPG pulse from at least a waveform parameter characterizing a shape of the individual PPG pulse;

assigning a weighting factor to each pulse, comprising calculating the weighting factor by using a weighting function comprising a mathematical operator inputted with said set of at least one venous pulse feature;

computing a weighted-average PPG pulse by using the individual PPG pulses and their respective weighting factors; and determining the physiological parameter by using the weighted-average PPG pulse.

18. A method for determining a physiological parameter, comprising the steps of:

providing a photoplethysmography (PPG) sensor device configured to measure a single PPG signal comprising a non-modulated component and a time-modulated component, wherein the time-modulated component comprises at least an arterial pulsatility component and a venous pulsatility component;

using the PPG sensor device to measure the single PPG signal on a user, the single PPG signal containing at least two cardiac cycles;

identifying individual PPG pulses from the single PPG signal, each individual PPG pulse corresponding to a cardiac cycle;

for each individual PPG pulse, determining a set of at least one venous-related feature indicative of the contribution of venous pulsatility to the time-modulated component of the individual PPG pulse from at least a waveform parameter characterizing a shape of the individual PPG pulse;

assigning a weighting factor to each pulse, comprising calculating the weighting factor by using a weighting function comprising a mathematical operator inputted with said set of at least one venous-related feature;

computing a weighted-average PPG pulse by using the individual PPG pulses and their respective weighting factors; and determining the physiological parameter by using the weighted-average PPG pulse;

wherein the weighted-average PPG pulse $p_{wa}(t)$ is calculated by:

$$p_{wa}(t) = \frac{\left[\sum_{k=1}^{K} w_k \cdot p_k(t)\right]}{\sum_{k=1}^{K} w_k}$$

where $p_k(t)$ represents the $k^{th}$ identified PPG pulse and $w_k$ is the weighting factor associated with the $k^{th}$ identified PPG pulse.

* * * * *